US011756653B2

(12) United States Patent
Van Aggelen

(10) Patent No.: US 11,756,653 B2
(45) Date of Patent: Sep. 12, 2023

(54) MACHINE LEARNING MODEL FOR PREDICTING MULTIDRUG RESISTANT GENE TARGETS

(71) Applicant: KONINKLIJKE PHILIPS N.V., Eindhoven (NL)

(72) Inventor: Helen Cecile Van Aggelen, Berkeley, CA (US)

(73) Assignee: Koninklijke Philips N.V., Eindhoven (NL)

(*) Notice: Subject to any disclaimer, the term of this patent is extended or adjusted under 35 U.S.C. 154(b) by 649 days.

(21) Appl. No.: 16/739,898

(22) Filed: Jan. 10, 2020

(65) Prior Publication Data

US 2020/0243163 A1 Jul. 30, 2020

Related U.S. Application Data

(60) Provisional application No. 62/793,433, filed on Jan. 17, 2019.

(51) Int. Cl.
    *G16B 40/00* (2019.01)
    *G16B 35/20* (2019.01)
    *G06N 20/00* (2019.01)
    *G06N 5/04* (2023.01)
    *G16B 30/00* (2019.01)

(52) U.S. Cl.
    CPC .............. *G16B 40/00* (2019.02); *G06N 5/04* (2013.01); *G06N 20/00* (2019.01); *G16B 30/00* (2019.02); *G16B 35/20* (2019.02)

(58) Field of Classification Search
    None
    See application file for complete search history.

(56) References Cited

U.S. PATENT DOCUMENTS

| | | | | |
|---|---|---|---|---|
| 10,192,026 | B2* | 1/2019 | Semenyuk | G16B 15/00 |
| 11,347,810 | B2* | 5/2022 | Kaufman | G06F 16/907 |
| 11,348,691 | B1* | 5/2022 | Kenedy | G06Q 40/00 |
| 2013/0332133 | A1* | 12/2013 | Horn | G16B 50/00 703/11 |
| 2016/0251648 | A1* | 9/2016 | Wang | C12N 15/63 506/10 |
| 2016/0259880 | A1* | 9/2016 | Semenyuk | G16B 15/00 |
| 2019/0087533 | A1* | 3/2019 | O'Hara | C12Q 1/689 |
| 2019/0177718 | A1* | 6/2019 | Church | C12Q 1/6869 |
| 2019/0330617 | A1* | 10/2019 | Church | C12Q 1/6844 |
| 2020/0056229 | A1* | 2/2020 | Mir | G01N 21/6428 |
| 2020/0203016 | A1* | 6/2020 | Hubbell | G16B 30/00 |
| 2020/0243163 | A1* | 7/2020 | Van Aggelen | G06N 20/00 |

(Continued)

OTHER PUBLICATIONS

Chuai, G. et al., "DeepCRISPR: optimized CRISPR guide RNA design by deep learning". Genome Biology (2018) 19:80.

(Continued)

*Primary Examiner* — Farhan M Syed

(57) ABSTRACT

A method of predicting a gene target sequence for a gene-modifying therapeutic, such as a CRISPR-based therapeutic, that includes the steps of determining a genomic dataset for one or more infectious bacterial samples isolated from one or more hospitals, and inputting the genomic dataset for the one or more infectious bacterial samples into a machine learning model to determine the presence of antimicrobial resistance genes.

10 Claims, 10 Drawing Sheets

Specification includes a Sequence Listing.

(56) References Cited

U.S. PATENT DOCUMENTS

2021/0090694 A1* 3/2021 Colley .................. G16B 40/00

OTHER PUBLICATIONS

Arango-Argoty, G. et al., "DeepARG: a deep learning approach for predicting antibiotic resistance genes from metagenomic data". Microbiome (2018) 6:23.
Beisel, C. et al., "A CRISPR design for next-generation antimicrobials". Genome Biology (2014), 15:516.
Kim, H.K. et al., "Deep learning improves prediction of CRISPR-Cpf1 guide RNA activity" Nature Biotechnology. Brief Communications. vol. 36, No. 3, Mar. 2018.

* cited by examiner

| Sequenceid | AccessionNumber | Name | Amikacin | Amoxicillin+k clavulanate | Amp/ sulbactam |
|---|---|---|---|---|---|
| 711eef99-4ca1-48e7-b36a-8254bdb71113 | B2F8367C-134E-4230-9A45-1D234ED2D850 | 5 | NaN | 1.0 | 1.0 |
| 2029bb2f-9bab-48d1-b0f4-02afad3db217 | D44FF7B7-C37E-4D39-948B-88F1571DC966 | 5 | NaN | 1.0 | 1.0 |
| c231b0ab-e088-45e0-ab29-de08309c01o8 | 458EB9C1-96ED-429E-A87F-E8B3CB6ED367 | 5 | NaN | 0.0 | 0.0 |
| e6f785ea-96a7-4139-8f65-ec30d64e0b8d | 1BB75731-3689-485C-BF17-D41FC01ED1CD | 2 | NaN | NaN | NaN |
| 8a0f5054-4c5c-4cde-8a2b-3ddcef92557c | 308F7E99-E3AD-4181-A7A4-75A18D4259ED | 5 | NaN | 0.0 | 0.0 |
| KPN301 | NaN | 3 | 0.0 | NaN | 0.0 |

| | Ampicillin | Azithromycin | Aztreonam | ... | 4398 | 1804 | 3427 | 4396 | 2003 | 2000 |
|---|---|---|---|---|---|---|---|---|---|---|
| | NaN | 0.0 | NaN | ... | 0 | 0 | 0 | 0 | 0 | 0 |
| | NaN | 0.0 | NaN | ... | 0 | 0 | 0 | 0 | 0 | 0 |
| | NaN | 1.0 | NaN | ... | 0 | 0 | 0 | 0 | 0 | 0 |
| | 0.0 | NaN | NaN | ... | 0 | 0 | 0 | 0 | 0 | 0 |
| | NaN | 0.0 | NaN | ... | 0 | 0 | 0 | 0 | 0 | 0 |
| | 0.0 | NaN | 0.0 | ... | 0 | 0 | 0 | 0 | 0 | 0 |

| Sequenceid | Amikacin | Ampicillin/ sulbactam | Ampicillin | Aztreonam | Cefazolin | Cefepime | Cefotaxime | Cefoxitin | Ceftazidime | ... | 882 | 89 |
|---|---|---|---|---|---|---|---|---|---|---|---|---|
| KPN2016 | 1.0 | 0.0 | 0.0 | 0.0 | 0.0 | 0.0 | 0.0 | 0.0 | 0.0 | ... | 0 | 0 |
| KPN294 | 0.0 | 0.0 | 0.0 | 0.0 | 0.0 | 0.0 | 0.0 | 0.0 | 0.0 | ... | 0 | 0 |
| KPN1740 | 1.0 | 0.0 | 0.0 | 0.0 | 0.0 | NaN | 0.0 | 1.0 | 0.0 | ... | 0 | 0 |
| KPN304 | 1.0 | 0.0 | 0.0 | 0.0 | 0.0 | 0.0 | 0.0 | 0.0 | 0.0 | ... | 0 | 0 |
| KPN1478 | 1.0 | 0.0 | 0.0 | 0.0 | 0.0 | 0.0 | 0.0 | 0.0 | 0.0 | ... | 0 | 0 |
| KPN669 | 1.0 | 0.0 | 0.0 | 0.0 | 0.0 | 0.0 | 0.0 | 0.0 | 0.0 | ... | 0 | 0 |
| KPN1942 | 1.0 | 0.0 | 0.0 | 0.0 | 0.0 | 0.0 | 0.0 | 1.0 | 0.0 | ... | 0 | 0 |
| KPN2088 | 1.0 | 0.0 | 0.0 | 0.0 | 0.0 | 0.0 | 0.0 | 0.0 | 0.0 | ... | 0 | 0 |
| KPN422 | 1.0 | 0.0 | 0.0 | 0.0 | 0.0 | NaN | 0.0 | 0.0 | 0.0 | ... | 0 | 0 |

FIG. 7

| Meropenem | Imipenem | Sequenceid |
|---|---|---|
| 0.0 | 0.0 | KPN553 |
| 0.0 | 0.0 | KPN1481 |
| 0.0 | 0.0 | KPN1844 |
| 0.0 | 0.0 | KPN1426 |
| 0.0 | 0.0 | KPN755 |
| 0.0 | 0.0 | KPN1458 |
| 0.0 | 0.0 | KPN1273 |
| 0.0 | 0.0 | KPN603 |
| 0.0 | 0.0 | KPN1145 |
| 0.0 | 0.0 | KPN528 |
| 0.0 | 0.0 | KPN1010 |
| 0.0 | 0.0 | KPN537 |
| 0.0 | 0.0 | KPN658 |

FIG. 8

MACHINE LEARNING MODEL FOR PREDICTING MULTIDRUG RESISTANT GENE TARGETS

INCORPORATION OF SEQUENCE LISTING

This application contains a sequence listing, which is contained on an ASCII text file entitled "Sequence Listing" (PHI 3051 Sequences_ST25, created Feb. 21, 2020, having a size of 8,361 bytes), which is herein incorporated by reference.

TECHNICAL FIELD

Various exemplary embodiments herein relate generally to a machine learning model that is trained to predict antibiotic resistance phenotypes of infectious bacteria based on genomic data. Various exemplary embodiments herein further relate generally to a machine learning model that may be utilized to predict gene targets for gene-modifying therapeutics.

BACKGROUND

The extensive use of antibiotics in medicine and agriculture coupled with a shortage of new antibiotics has given rise to an antibiotic resistance crisis, in which several pathogens are becoming resistant to treatment. Hospital-acquired infections are a big concern for both hospitals and patients, especially when the infection involves a multi-drug resistant pathogen. Not only do hospital-acquired infections put patients at risk, they also put a big financial and reputational burden on the hospital and health care system.

Since few new antibiotic treatments are being developed, there has been a revival in phage therapy research, in which bacteriophages are used to kill bacteria. Lytic phages can kill bacteria by breaking them open to release their own genetic material. But they are typically highly specific to the bacterial target and are therefore more difficult to employ in routine clinical settings. It can be challenging to find and isolate the right phage for a patient's infection. More recently, CRISPR-based gene-modification approaches have been explored.

In order to use CRISPR-based antimicrobial therapies in a clinical setting, appropriate targets, i.e., CRISPR RNA-sequences, would have to be determined through genomic analysis. The challenge presented is anticipating which resistant bacteria will occur in the hospital, and selecting sequences that are specific to the bacteria that are difficult to treat or drug-resistant, so that more benign and commensal bacterial strains are not affected.

A method is needed to assist in determining specific gene targets to optimize these CRISPR-based therapies.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to a method of predicting a gene target sequence for a gene-modifying therapeutic, such as CRISPR-based therapeutic, that includes the steps of determining a genomic dataset for one or more infectious bacterial samples isolated from one or more hospitals, wherein the genomic dataset includes genomic sequences of the infectious bacterial samples, and inputting the genomic dataset for the one or more infectious bacterial samples into a machine learning model to determine the presence of antimicrobial resistance genes. The machine learning model includes a machine learning algorithm which produces a first set of k-mers by k-merizing the genomic sequences contained in the genomic dataset, determines whether the first set of k-mers indicates the presence of an antimicrobial resistance genes, maintains a log of which genomic sequences contain antimicrobial resistance genes, further k-merizes the genomic sequences that contain antimicrobial resistance genes into a second set of k-mers having a predetermined length, determines whether the k-mers of predetermined length are shared by any of the samples in the genomic dataset, compares the shared k-mers of predetermined length to one or more non-multidrug resistant whole bacterial genomes and retrieves a target sequence comprising the k-mer of predetermined length.

Various embodiments relate to a method of predicting a gene target sequence for a gene-modifying therapeutic wherein the genomic dataset is a whole bacterial genome sequence dataset in a FASTQ or FASTA format.

Various embodiments relate to a method of predicting a gene target sequence for a gene-modifying therapeutic wherein the machine learning model determines whether the first set of k-mers indicates the presence of an antimicrobial resistance gene by comparing the k-mers to a known antimicrobial resistance gene database.

Various embodiments relate to a method of predicting a gene target sequence for a gene-modifying therapeutic, wherein the second set of k-mers of predetermined length is an 11-mer, 12-mer, 13-mer, 14-mer or 15-mer.

Various embodiments further relate to method of predicting a gene target sequence for a gene-modifying therapeutic, wherein the machine learning model further identifies a gene-modifying therapeutic or phage therapy to target the target sequence.

BRIEF DESCRIPTION OF THE DRAWINGS

In order to better understand various exemplary embodiments, reference is made to the accompanying drawings, wherein:

FIG. 4 is an extract of an exemplary embodiment of a data table generated by the machine learning model with gene information and antibiotic susceptibility test results for a subset of tested drugs;

FIG. 7 is an extract of an exemplary embodiment of a data table with gene information and AST results for a *Klebsiella pneumoniae* data set;

FIG. 8 is an exemplary embodiment of a data table generated by the machine learning model showing samples with selected genes that are resistant to meropenem and imipenem.

DETAILED DESCRIPTION

Figure 1:
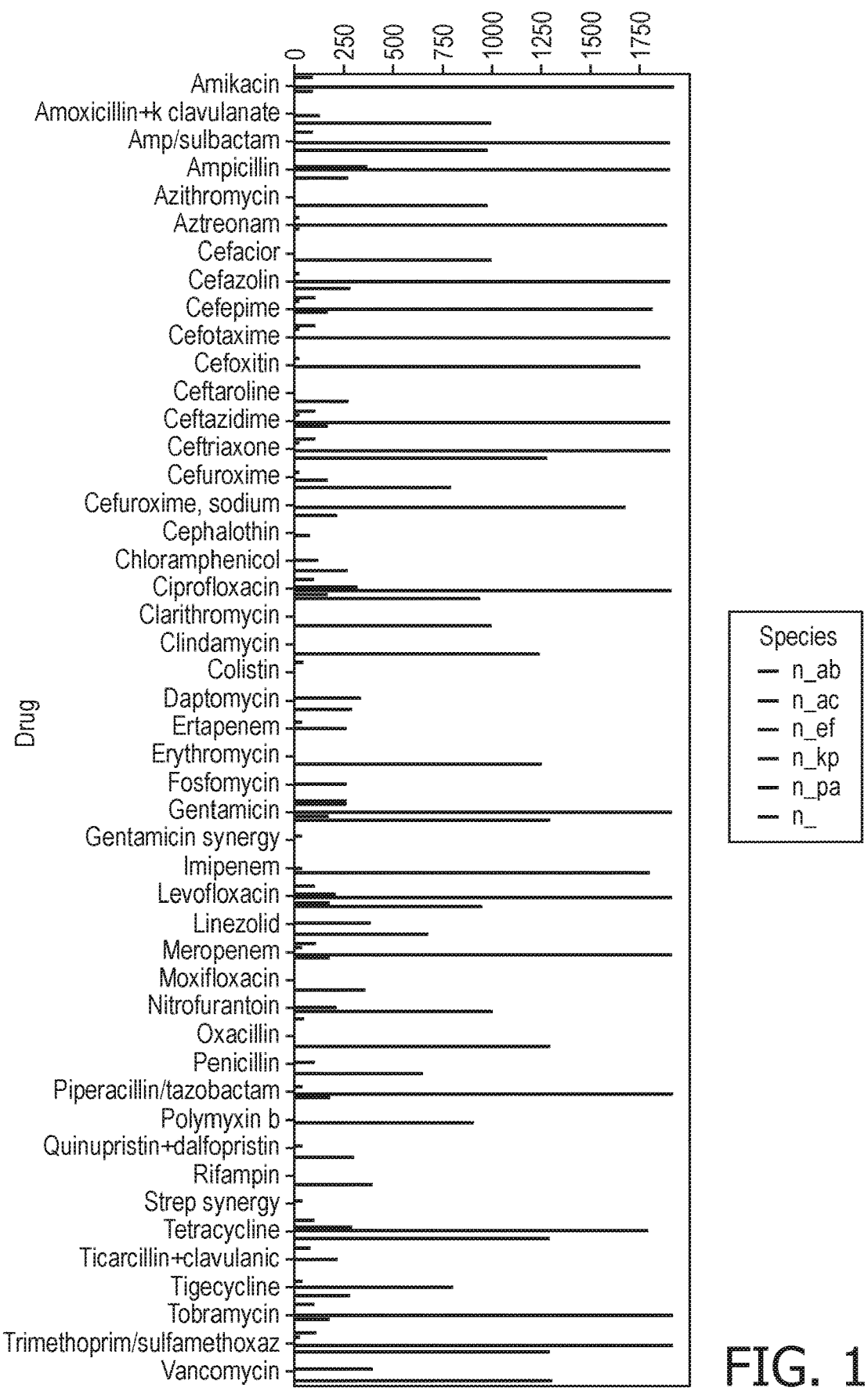
FIG. 1 is a graph of the number of samples for each species used to train the machine learning model plotted against the antibiotic susceptibility test results.

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

Experimental methods to determine the drug susceptibility of bacteria are typically slow, requiring around 3-7 days to culture the bacterium and measure its response to different drug concentrations. Patients typically receive an empirical treatment until the results from these tests come back from the lab. This empirical treatment may not always be effective, and valuable time may be lost due to ineffective therapy. As genomic analysis becomes more common in the clinical environment (the cost of whole genome analysis for bacteria has dropped to around $50-200 per sample), a prediction of the pathogen's drug resistances based on its genome can help drive down the time to appropriate treatment and provide insight into resistance mechanisms. Knowledge of resistance mechanisms can inform choice of therapy (e.g., resistance due to efflux mechanisms vs. resistance due to production of beta lactamases), drive stewardship programs and infection control.

Antimicrobial resistance (AMR) is not always straightforward to predict from genomic data. For some drugs, the presence of a particular gene maps nearly one-to-one with resistance, and most of the genomic work has concentrated on these genes. However, for many drugs, the phenotypic effect is not that easily predicted from genomic data. This type of problem can be solved with machine learning models. Such models do not need to start from gene presence information, as they can use raw sequence data input.

In a first aspect, the present disclosure provides a machine learning model that may be trained to predict the antibiotic resistance phenotype of an infectious bacterial sample based on genomic data.

In various embodiments, the machine learning model may be trained using genomic data and clinical data from a plurality of clinical sites.

In various embodiments, the clinical data may be obtained from clinical sites selected from a group that includes a single hospital, clinic or healthcare facility, or a group of hospitals, clinics, or healthcare facilities in a particular region.

In various embodiments, genomic data used to train the model may include whole or partial bacterial genome DNA or RNA sequence reads in a suitable format, including a FASTQ or FASTA format.

In various embodiments, suitable clinical data that may be used to train the model include antibiotic susceptibility test (AST) results in the form of minimum inhibitory concentration (MIC) values, resistant/intermediate/susceptible (S/I/R) labels and the like. Additional clinical data that may be added to the model include the species name of the infectious bacteria, sample source type (blood, urine, etc.), and sample body site (skin, lung, etc.).

The machine learning model may further be trained using antimicrobial resistance (AMR) gene sequence data, wherein the AMR gene presence or absence is utilized as an input feature. In various embodiments, the AMR genes may first be detected in the genomic data. In one embodiment, a fast k-mer (k=31) based method may be used to scan whole bacterial genome DNA sequence reads in FASTQ format for the presence of known AMR genes or sequences disclosed in an existing AMR database. Such method may be used in combination with a data structure configured to determine which specific genes (alleles) are observed. The data structure may be built for the AMR genes disclosed in the existing database by calculating a k-mer based similarity metric between the genes, clustering them, and determining several levels of gene similarity based on predefined thresholds.

In various embodiments, the data structure may be in the form a tree-based structure, or another data structure that indicates a hierarchical relationship between groups of one or more genes.

In various embodiments, the detected AMR genes may be summarized in a visual format, including a table or binary encoding, with results, such as gene absence or presence, described using a predefined representation symbol. Suitable representation symbols include numbers, letters, and the like. Preferred visual formats include a table format, as substantially shown in FIGS. 4 and 7.

In various embodiments, the machine learning model may be configured to look at genomic features associated with multidrug resistance. In such embodiment, each sample may be assigned a risk representation such as a risk score.

In other embodiments, the machine learning model may be configured to look at genomic features associated with known classes of progressing drug resistance, such as resistance to specific drug candidates. Preferred specific drug candidates include last-resort drugs such as carbapenems.

The machine learning model of the present disclosure may be any type of machine learning model, including Support Vector Machines (SVM), Naïve Bayes machines, Maximum Entropy, logistic regression, and/or linear regression models and artificial neural networks. The embodiments described below use SVM models.

In some embodiments, the machine learning model may be trained to predict the antibiotic susceptibility profile for future infectious bacterial samples isolated from one or more hospitals.

In some embodiments, the machine learning model may be trained to predict which genomic sequences, mutations, or new genes may occur in a hospital at a future date. In some embodiments, genomic information from other hospitals or sites (e.g., other hospitals in the region or the same network) may be used to make the prediction, as shown in FIG. 6.

Figure 6:
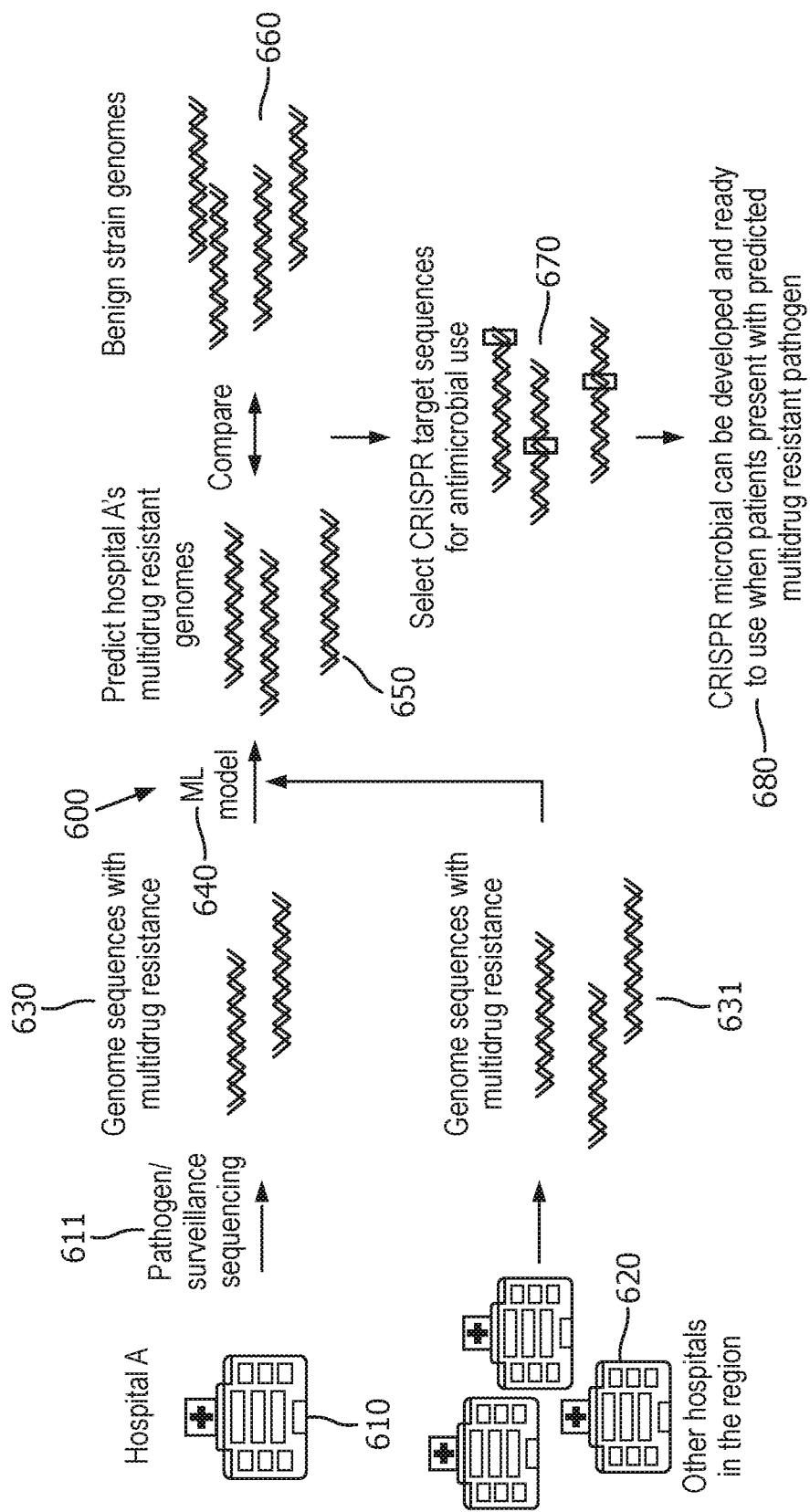
FIG. 6 is a flow diagram illustrating a system to suggest hospital-specific CRISPR-based antimicrobial targets.

FIG. 6 shows a flow diagram 600 describing hospital A 610, which, through a step of pathogen and surveillance sequencing 601, collects a dataset of genome sequences with multidrug resistance 630. The flow diagram 600 further shows other hospitals in the region 620 also determining a collection of genome sequences with multidrug resistance 631. The dataset of genome sequences with multidrug resistance 630 for both first hospital A 610 and other hospitals 620 may be collected by determining the whole genome sequences of one or infectious bacterial samples that show multidrug resistance when subjected to antibiotic susceptibility testing. The multidrug resistant genome sequences 630,631 from hospital A 610 and the other hospitals 620 are then inputted into a machine learning model 640.

The machine learning model 640 first k-merizes the genome sequences 630,631 taken from hospital A 610 and the other hospitals 620 and determines whether the k-mers indicate the presence of any AMR genes by comparing the k-mers to an AMR gene of interest that may be identified using an external database. The machine learning model 640 then generates a prediction of future multidrug resistant genomes 650 in hospital A 610.

In some embodiments, the machine learning model may be further utilized to compare the predicted multidrug resistant genomes 650 to the genomes of benign bacterial strains 660 and select and/or suggest gene target sequences for antimicrobial use 670. A gene-modifying antimicrobial therapeutic may then be developed in a next step 680 and ready to use when a patient presents with a predicted multidrug resistant pathogen.

Accordingly, in another aspect, the present disclosure provides an embodiment of the machine learning model, wherein the machine learning model may be utilized to suggest multidrug resistant gene targets for gene modification therapeutics.

In various embodiments, the gene modification therapeutic may include a CRISPR-based therapeutic. In some embodiments, the CRISPR-based therapeutic may include a phage or phagemid-based therapeutic engineered to encode a Cas-9 nuclease, a CRISPR-RNA sequence and a trans-activating crRNA for CRISPR RNA processing. The CRISPR-RNA sequence may be specific for the multidrug resistant target, wherein the phage may be utilized as a delivery mechanism into a bacterial cell. The CRISPR sequences may also be cloned into phagemids and delivered by phages or delivered by plasmids.

Example 1

Training the Machine Learning Model to Predict Antibiotic Resistance Phenotypes

In an exemplary embodiment, genomic and clinical data from three different clinical sites were used to train and evaluate an SVM model. The genomic data consisted of whole bacterial genome DNA sequencing reads in FASTQ format, in the form of Illumina 2×150 bp reads. The clinical data was used to train the model and consisted of antibiotic susceptibility test (AST) results in the form of minimum inhibitory concentration (MIC) values or resistant/intermediate/susceptible (S/I/R) labels.

In total, the dataset contained 3828 samples belonging to the ESKAPE species (*Enterococcus faecium, Staphylococcus aureus, Klebsiella pneumoniae, Acinetobacter baumannii, Pseudomonas aeruginosa, Enterobacter cloacae*). The number of samples varied per species, with *Staphylococcus* and *Klebsiella* being the most abundant, as shown in FIG. 1. The drugs tested on each sample varied as some drugs were more commonly included in an AST panel than others with AST panels varying in composition per clinical site. The number of samples for each species and drug test are shown in FIG. 1.

The input features for the model were the sample's presence or absence of genes associated with AMR. The AMR genes inputted into the model were generated from the NCBI AMR gene database. The AMR genes were first detected using a fast k-mer (k=31) based method to scan the FASTQ reads for the presence of the AMR genes/sequences in the NCBI AMR database, in combination with a tree-based data structure to determine which specific genes (alleles) were observed. The tree-based structure for the NCBI AMR was configured to define several levels of similarity between genes based on how proximate the genes were to each other in the tree.

For every sample in the dataset, the AMR genes were detected with this method and summarized in table format, as exemplified in FIG. 7, to serve as model input. The AST results for the same samples were added as columns to the table. Species name and other clinical data such as specimen type or body location were added as additional columns. The AST results were the target features and were used in the form of a binary encoding. S/I labels were encoded as a "1" and R labels were encoded as "0". The encoding essentially represented whether a sample was resistant to a drug. The input features were the gene data and potential clinical data.

To train and test the model, the samples were randomly divided into train and test sets. 5-fold cross-validation was performed to make sure the model was not over-trained. An SVM model was used to predict the antibiotic susceptibility for each drug in the form of a binary classification (susceptible/non-susceptible).

Figure 2:
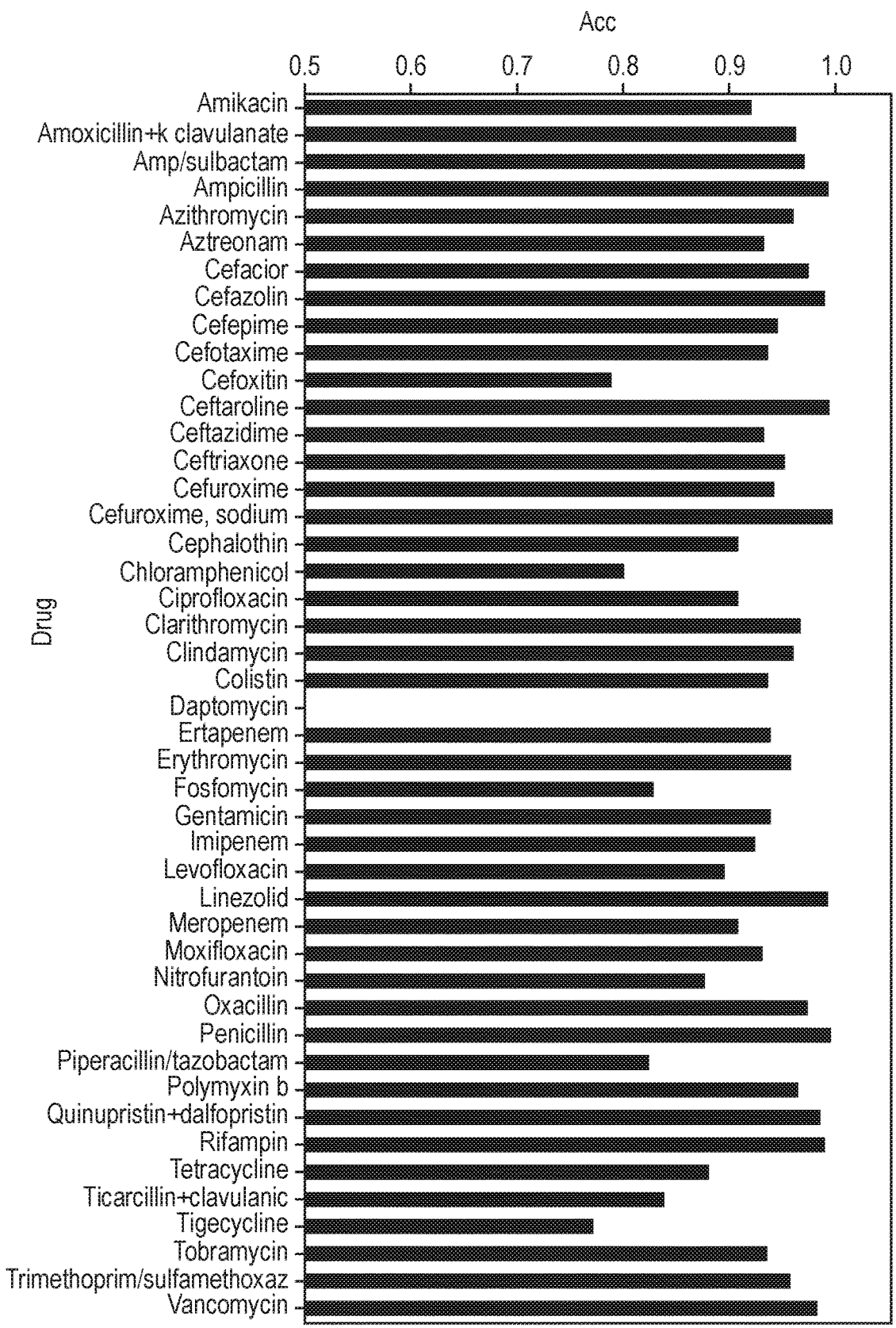
FIG. 2 is a graph that illustrates the accuracy of a support vector machine (SVM) model for antibiotic susceptibility prediction from gene presence and absence parameters.
Figure 3:
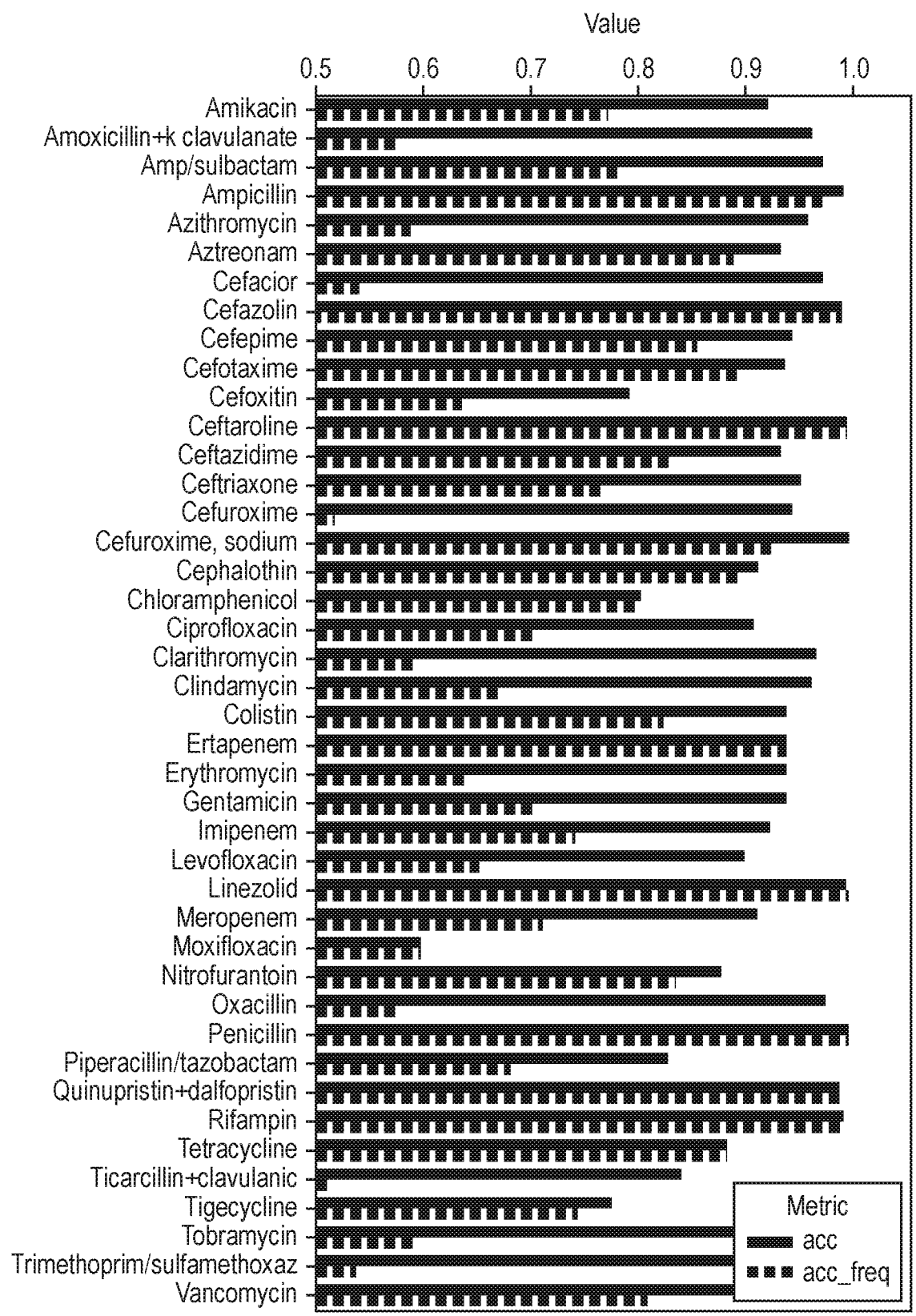
FIG. 3 is a graph that shows the performance of a support vector machine (genomics-based) model compared to a prediction based on the dominant data label.

For the exemplary dataset, the SVM model reached an average accuracy over all drugs of about 93%. The accuracy differed per drug, but for many drugs, an accuracy well over 90% was achieved, as shown in FIG. 2. For daptomycin, there were not enough data points in the susceptible or non-susceptible class to make a model. The exemplary model was found to be significantly more accurate for most drugs than a dominant label prediction as shown in FIG. 3.

Example 2

Example Data and Code Extract for Training the Machine Learning Model

Software was developed to build the machine learning model of Example 1 and evaluate it.

A table was loaded in a format as shown in FIG. 4. In FIG. 4, the columns with drug names indicate whether the sample is susceptible (entry 1) or non-susceptible (entry 0). The last columns indicate the gene presence (entry 1) or absence (entry 0). The genes are indicated with numbers in the column headers, which refer to their gene names in the database.

In total, the table contained 3828 rows and 899 columns—45 columns for the different drugs and 850 columns for the genes.

The table was then separated into an input matrix X and a target matrix Y. The input consisted of the gene presence or absence data and the target contained the AST results in susceptible/non-susceptible form.

The samples that were not tested for the drug were then removed. An SVM classification model was then built. To measure performance of the model, the model was trained with a 5-fold cross-validation (k=5) and the mean accuracy and standard deviation returned (across the 5 folds) for each drug. Then the model was executed.

Only gene information was used in the exemplary model with no species information. The exemplary model performed well even without the species information. For certain drugs (daptomycin, fosfomycin, polymyxin b, gentamicin synergy), no model could be trained because there were not sufficient data points in the "susceptible" and "non-susceptible" datasets. For these drugs, the accuracy and standard deviation arrays had hard zero entries.

These were excluded when computing the average accuracy and standard deviation over all drugs.

Figure 5:
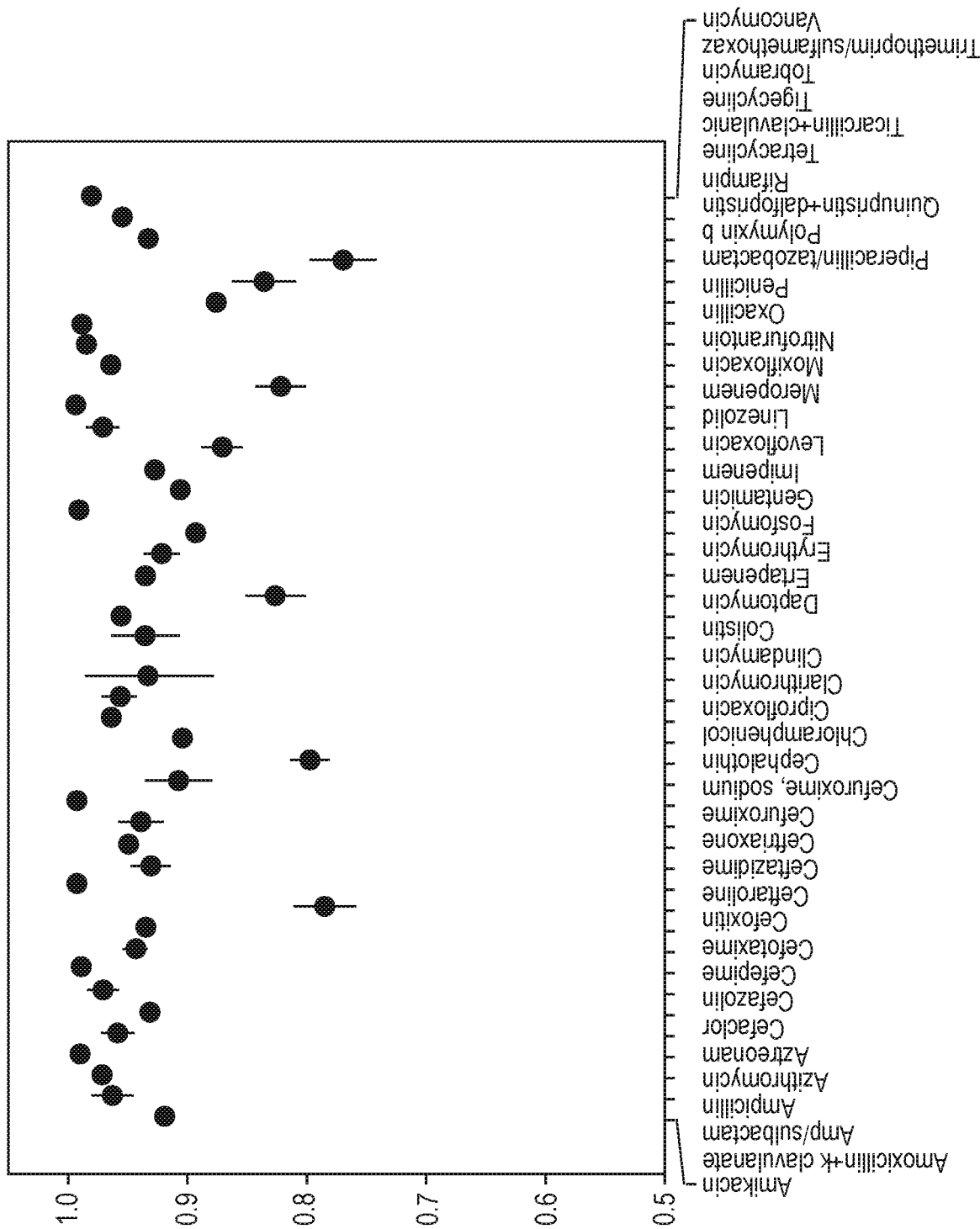
FIG. 5 is a graphical plot of the accuracies and standard deviations for each drug tested in the model.

The accuracies and standard deviations were plotted for all drugs as shown in FIG. 5. For many of the drugs, the accuracy was greater than 90% with little variance. Significant differences in performance per iteration were only seen for a few drugs, largely due to a small sample set for those drugs. For example, for the colistin entry with the highest variance, there were not enough samples to train the model.

Example 3

Suggestion of Site-Specific CRISPR-Cas Targets for Antimicrobial Use

In this example, a method of identifying potential CRISPR-Cas targets for antimicrobial use is illustrated using a public *Klebsiella* data set obtained from Houston Methodist Hospital.

Step 1

A determination of which high-risk bacteria were 1) common to the hospital, and 2) could be expected to appear in the hospital in the future, was made using the machine learning model of Example 1.

As test data, a sample from a published *Klebsiella pneumoniae* data set was used. The data set was collected in Houston Methodist Hospital between 2011 and 2015 and contained mostly multidrug resistant sample data. Next, AMR genes in the data set were detected.

The results were collected in table form as shown in FIG. 7. In the table, each sample is shown in its own row and the columns represent susceptibility typing results (I/O for susceptible/non-susceptible) and the genes detected in the sample (I/O for gene presence/absence). The gene names are encoded with numbers (e.g., the column 882). The table contained 1646 rows and 508 columns, corresponding to 24 drugs and 483 genes.

To determine which "high-risk" organisms and genomic features were expected in the hospital, two options were explored: 1) genomic features associated with drug resistance; and 2) genomic features associated with known classes of progressing drug resistance, such as carbapenem resistance or vancomycin resistance.

To look at genomic factors associated with multidrug resistance, each sample was assigned a risk score, calculated as a fraction of AST results that returned as non-susceptible (a 0 in the table), using the code below. The fraction is computed based on the available drug tests ("NaN" entries are ignored). For each gene column, the average risk score was then computed across all samples that contained the gene. The genes having an average risk score of greater than 0.9 over all samples that contained the gene were selected.

These calculations lead to the following genes:
gene 1176—risk: 0.9545454545454546
gene 128—risk: 0.9545454545454546
gene 1542—risk: 0.9545454545454546
gene 162/564/2537—risk: 0.907070707070707
gene 280/319/856/969/1033/1294/1368/1522/1861/1970/2031/2164/2188/2196/2331/2708/3042/3105/3186/3397/3563/3761/4025/4563—risk: 0.9171744620114186
gene 329/508/560/666/1040/1752/1902/1925/1996/2303/2394/2421/2822/3253/3373/3571/3758/3842/3847/3854/4227/4277/4344—risk: 0.9545454545454546
gene 3548—risk: 0.9172206252245779
gene 517—risk: 0.9084556747600225

The outputted gene names referred to entries in the NCBI database and correspond to different types of resistance as shown below:

```
1176 0.95 - srm(B) /// efflux
128 0.95 - car(A) /// macrolide resistance
1542 0.95 - blaOXA /// beta lactam resistance
162/564/2537 0.91 - blaADC /// cephalosporin resistance
280/319/856/969/1033/1294/1368/1522/1861/1970/2031/2164/2188/2196/
2331/2708/3042/3105/3186/3397/3563/3761/4025/4563 0.92 - blaNDM ///
beta lactam resistance
3548 0.92 - blaOXA /// beta lactam resistance
517 0.91 - rmtF /// aminoglycoside resistance
```

The high-risk genes were alternatively selected using a machine learning model that predicted the risk score based on gene content. From this model, the genes associated with a high risk factor were examined.

The gene labeled 280/319/856/969/1033/1294/1368/1522/1861/1970/2031/2164/2188/2196/2331/2708/3042/3105/3186/3397/3563/3761/4025/4563, which is an NDM gene associated with beta lactam resistance, was chosen as a target. 13 samples were found to contain the gene, which were all resistant to imipenem and meropenem, as shown in FIG. 8. The phenotype prediction model described in Example 1 was used to indicate which genes in the samples caused meropenem resistance. The phenotype prediction model was trained on the 13 sample dataset.

The resulting model was then applied to meropenem. The most important genes that lead to non-susceptible and susceptible classifications were extracted in the model for meropenem and the results were plotted as shown in FIG. 9.

Figure 9:
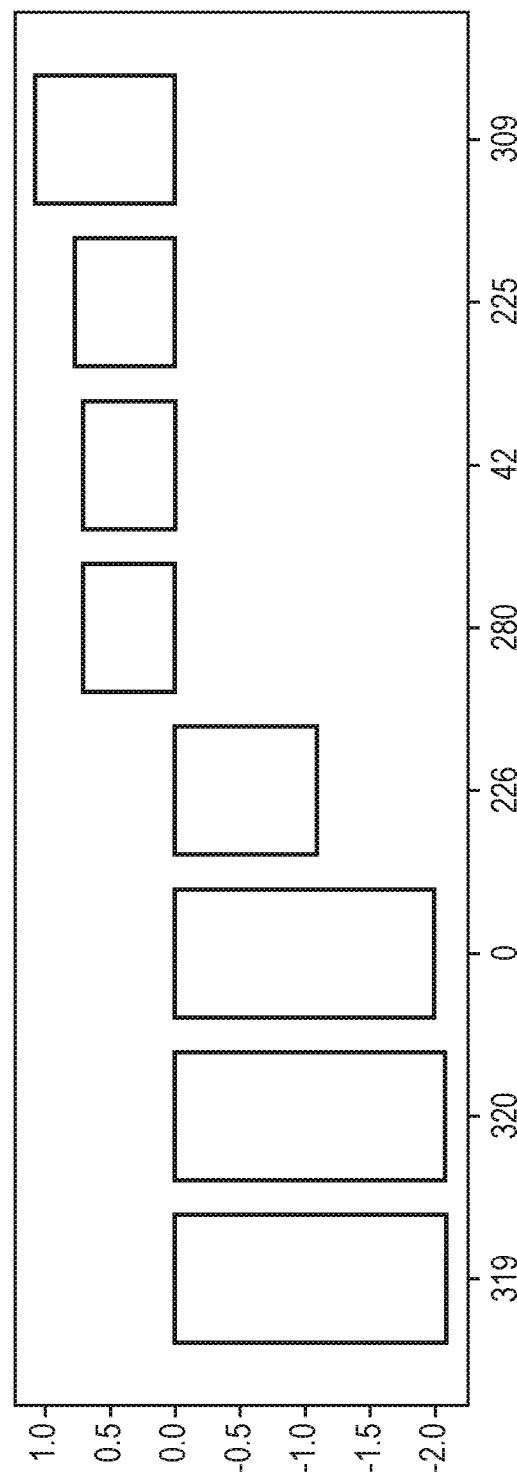
FIG. 9 is a graph showing code output for the most important genes associated with non-susceptibility and susceptibility in the SVM model.

The genes associated most strongly with resistance in the SVM model were identified as KPC genes, shown in FIG. 9 as index numbers 319, 320 and 0, and NDM genes, shown in FIG. 9 as index number 226. The NDM gene was identified as an important target for multidrug resistance and specifically carbapenem resistance in the hospital pathogen population. This target was chosen for further evaluation.

Step 2

Based on the set of pathogens of interest and their associated genomic drug resistance factors, genomic target sequences that were appropriate for antimicrobial therapy were selected in this step.

The code used in this step determined the presence of AMR genes by k-merizing the reads, determining whether the k-mers indicated the presence of any of the AMR genes supplied, and keeping a log of which reads were hits to the AMR gene. To start gathering genomic targets for CRISPR/Cas, the code grabbed the reads that were hits to the gene of interest, i.e., the NDM gene of index number 226. The code was applied to all of the 13 samples that contained the gene. Sample read information was used (instead of NCBI gene references) so that any deviations in the samples from the reference genes could be identified.

For each sample, the code then k-merized the reads into 11-mers. The genomic targets for the CRISPR/Cas system were determined to be around 23 bases long, including PAM sequences. However, a substring of 11-mers was used to configure the guides to be perfect matches at least to the 8-12 bases closest to the PAM sequence. The PAM sequence was assumed to be "NGG". The code was configured to look for 9-mers preceded by "CC" or followed by "GG".

Next, the set of 11-mers shared by all 13 samples was determined by gathering the 11-mers from all sample files and counting in how many samples they occurred. An 11-mer and its reverse complement were treated equally and only the smallest lexicographically was kept. From the output, only those 11-mers that appeared in all 13 samples were selected. 979 11-mers were returned.

From the above sample, the code identified 11-mers starting with "CC" (the reverse complement of the PAM sequence) or ending with "GG". This yielded 159 11-mers which could be valid targets that would work on all samples found in the hospital.

To ensure that the targets would not have off-target effects on benign or useful bacterial flora, the code then cross-checked the 11-mers against an *E. coli* genome that was not multidrug resistant. The *E. coli* genome was 11-merized and the same Python code was used to count how many times the potential target 11-mers appeared in the *E. coli* genome. Those 11-meres were tagged with a "0" count. 21 11-mers shown in Table 1 below were yielded as potential target sequences:

TABLE 1

11-mer Sequences.

| 11-mer Sequence Identifier | 11-mer Sequence | Count |
| --- | --- | --- |
| SEQ ID NO: 1 | CCAATCGTCGG | 0 |
| SEQ ID NO: 2 | CCCCGATAGCC | 0 |
| SEQ ID NO: 3 | CCATGGCTGAC | 0 |
| SEQ ID NO: 4 | CCCAAGGCCAG | 0 |
| SEQ ID NO: 5 | CCCATCTTGTC | 0 |
| SEQ ID NO: 6 | CCTTGGGGAAC | 0 |
| SEQ ID NO: 7 | CCCTCTTGCGG | 0 |
| SEQ ID NO: 8 | CCCCAAGGCCA | 0 |
| SEQ ID NO: 9 | CCCCGGCCACA | 0 |
| SEQ ID NO: 10 | ATAATATTGGG | 0 |
| SEQ ID NO: 11 | CCCCGAAACCC | 0 |
| SEQ ID NO: 12 | CCCAATCTGCC | 0 |
| SEQ ID NO: 13 | CCAAGTCGCTC | 0 |
| SEQ ID NO: 14 | CCGACACTGAG | 0 |
| SEQ ID NO: 15 | CCCGCATGGCC | 0 |
| SEQ ID NO: 16 | ATCGGGGCGG | 0 |
| SEQ ID NO: 17 | CCTAGTAAATA | 0 |
| SEQ ID NO: 18 | CCTATCTCGAC | 0 |
| SEQ ID NO: 19 | CCGGCCACACC | 0 |
| SEQ ID NO: 20 | AAGGATCGCGG | 0 |
| SEQ ID NO: 21 | CCGTTGGAAGC | 0 |

The full 23-bp target sequences corresponding to the 11-mers were then retrieved from the set of reads. The sample reads were k-merized together into 23-mers in a data file. The 11-mer targets were collected in a data file. Then the 23-bp target sequences were found that started or ended with the right PAM sequence that occurred in most of the reads. This was done by sorting and grabbing the highest 23-mer count. Then the occurrence of the 11-mer and its reverse complement were checked for.

This yielded the 23 mers shown in Table 2 below, along with the number of times they occurred in the reads from all samples:

TABLE 2

23-mer Sequences.

| 23-mer Sequence Identifier | 23-mer Sequence | Count |
| --- | --- | --- |
| SEQ ID NO: 22 | CCGACGATTGGCCAGCAAATGGA | 716 |
| SEQ ID NO: 23 | CCCCGATAGCCGCGCCGCAATCA | 425 |
| SEQ ID NO: 24 | CCATGGCTGACCACGTCACCCCC | 171 |
| SEQ ID NO: 25 | ATCACGATCATGCTGGCCTTGGG | 567 |
| SEQ ID NO: 26 | CACGCGCATCAGGACAAGATGGG | 653 |
| SEQ ID NO: 27 | CCTTGGGGAACGCCGCACCAAAC | 675 |
| SEQ ID NO: 28 | AACCAGCTTGCCCCGCAAGAGGG | 730 |
| SEQ ID NO: 29 | CCCCAAGGCCAGCATGATCGTGA | 567 |
| SEQ ID NO: 30 | CCCCGGCCACACCAGTGACAATA | 607 |
| SEQ ID NO: 31 | CCCAATATTATGCACCCGGTCGC | 559 |
| SEQ ID NO: 32 | CCCCGAAACCCGGCATGTCGAGA | 692 |
| SEQ ID NO: 33 | AAATCGCGCGATGGCAGATTGGG | 162 |
| SEQ ID NO: 34 | ACCGAGATTGCCGAGCGACTTGG | 733 |
| SEQ ID NO: 35 | CCGACACTGAGCACTACGCCGCG | 616 |
| SEQ ID NO: 36 | CCCGCATGGCCGACAAGCTGCGC | 317 |
| SEQ ID NO: 37 | CCGCCCCGATAGCCGCGCCGCA | 445 |
| SEQ ID NO: 38 | ATTAAGATCATCTATTTACTAGG | 438 |
| SEQ ID NO: 39 | CCTATCTCGACATGCCGGGTTTC | 691 |
| SEQ ID NO: 40 | CCGGCCACACCAGTGACAATATC | 601 |
| SEQ ID NO: 41 | CCGCGATCCTTCCAACTCGTCGC | 99 |
| SEQ ID NO: 42 | CCGTTGGAAGCGACTGCCCCGAA | 647 |

The methods described herein allow a computer to predict phenotypic antimicrobial resistance using genomic data. The methods of the invention are an improvement on other computer-based methods used to identify antimicrobial resistance, wherein the methods and machine learning model of the invention can predict the presence, as well as identify the sequence of particular genes in multidrug resistant infectious bacterial samples that may not map one-to-one with antimicrobial resistance.

The embodiments described herein may be implemented as software running on a processor with an associated memory and storage. The processor may be any hardware device capable of executing instructions stored in memory or storage or otherwise processing data. As such, the processor may include a microprocessor, field programmable gate array (FPGA), application-specific integrated circuit (ASIC), graphics processing units (GPU), specialized neural network processors, cloud computing systems, or other similar devices.

The memory may include various memories such as, for example L1, L2, or L3 cache or system memory. As such, the memory may include static random-access memory (SRAM), dynamic RAM (DRAM), flash memory, read only memory (ROM), or other similar memory devices.

The storage may include one or more machine-readable storage media such as read-only memory (ROM), random-access memory (RAM), magnetic disk storage media, optical storage media, flash-memory devices, or similar storage media. In various embodiments, the storage may store instructions for execution by the processor or data upon with the processor may operate. This software may implement the various embodiments described above.

Further such embodiments may be implemented on multiprocessor computer systems, distributed computer systems, and cloud computing systems. For example, the embodiments may be implemented as software on a server, a specific computer, on a cloud computing, or other computing platform.

Any combination of specific software running on a processor to implement the embodiments of the invention, constitute a specific dedicated machine.

As used herein, the term "non-transitory machine-readable storage medium" will be understood to exclude a transitory propagation signal but to include all forms of volatile and non-volatile memory.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A computer-implemented method of predicting a gene-modifying therapeutic effective against a gene target sequence from a bacterial sample using a system comprising a) a processor with an associated memory and storage and b) an external database, wherein the system is configured to execute a machine learning algorithm, the method comprising:

determining a genomic dataset for a first infectious bacterial sample isolated from a first hospital and at least one second infectious bacterial sample, wherein the genomic dataset comprises a first genomic sequence of the first infectious bacterial sample and a second genomic sequence from each second infectious bacterial sample; and inputting the genomic dataset comprising the first and the second genomic sequences the system;

executing the machine learning algorithm on the system, wherein the machine learning algorithm:

produces a first set of k-mers by k-merizing the first and the second genomic sequences contained in the genomic dataset;

determines whether the first set of k-mers indicates the presence of an antimicrobial resistance gene;

maintains a log identifying at least one genomic sequence in the genomic dataset as containing antimicrobial resistance genes;

further k-merizes the at least one identified genomic sequence into a second set of k-mers having a predetermined length;

determines whether the k-mers having the predetermined length are shared by multiple genomic sequences in the genomic dataset;

compares the shared k-mers having the predetermined length to one or more non-multidrug resistant whole bacterial genomes to identify a selected k-mer of predetermined length, wherein the non-multidrug resistant whole bacterial genomes are in the external database;
retrieves the gene target sequence, wherein the gene target sequence comprises the selected k-mer of predetermined length; and
identifying the gene-modifying therapeutic effective against the gene target sequence, wherein identifying the gene-modifying therapeutic further comprises:
analyzing bacterial samples isolated from one or more hospitals,
predicting, using the machine learning model, the occurrence of at least one of a genomic sequence, a mutation, and one or more new genes that may occur in the hospital, wherein the machine learning model is a support vector machine model, and
generating an antibiotic susceptibility profile.

2. The method of claim 1, wherein the genomic dataset is a dataset selected from the group consisting of a whole bacterial genome sequence dataset, a partial bacterial genome sequence dataset and an RNA sequence dataset.

3. The method of claim 1, wherein the genomic dataset is in a format selected from the group consisting of FASTQ and FASTA.

4. The method of claim 1, wherein each k-mer in the second set of k-mers is an 11-mer, 12-mer, 13-mer, 14-mer or 15-mer.

5. The method of claim 1, wherein the gene-modifying therapeutic is a CRISPR-based therapeutic.

6. The method of claim 1, wherein the gene-modifying therapeutic is a phage therapy to target the target sequence.

7. The method of claim 6, wherein the phage therapy is a CRISPR-based phage therapy.

8. A method of treating a patient infected by a bacterial agent having multidrug resistance, the method comprising:
determining a genomic dataset for a first infectious bacterial sample of the bacterial agent, wherein the genomic dataset comprises a first genomic sequence of the first infectious bacterial sample and at least one second genomic sequence;
inputting the genomic dataset comprising the first and the second genomic sequences into a system configured to execute a machine learning algorithm;
using the machine learning algorithm on the system to identify a gene target sequence in the first genomic sequence, wherein the machine learning algorithm:
produces a first set of k-mers by k-merizing the first and the second genomic sequences contained in the genomic dataset;
uses the first set of k-mers to detect the presence of an antimicrobial resistance gene in the first genomic sequence;
further k-merizes the first genomic sequence into a second set of k-mers having a predetermined length;
identifies shared k-mers having the predetermined length, wherein each shared k-mer is shared by the first genomic sequence and at least one second genomic sequence;
compares the shared k-mers having the predetermined length to one or more non-multidrug resistant whole bacterial genomes to identify a selected k-mer of predetermined length; and
retrieves the gene target sequence, wherein the gene target sequence comprises the selected k-mer of predetermined length;
identifying a gene-modifying therapeutic effective against the gene target sequence, wherein identifying the gene-modifying therapeutic further comprises:
analyzing bacterial samples isolated from one or more hospitals,
predicting, using the machine learning model, the occurrence of at least one of a genomic sequence, a mutation, and one or more new genes that may occur in the hospital, wherein the machine learning model is a support vector machine model, and
generating an antibiotic susceptibility profile; and
administering the gene-modifying therapeutic to the infected patient.

9. The method of claim 8, wherein the gene modifying therapeutic is a CRISPR-based therapeutic.

10. The method of claim 8, wherein the gene modifying therapeutic is a CRISPR-based phage therapy.

* * * * *

```
                              SEQUENCE LISTING

<160> NUMBER OF SEQ ID NOS: 42

<210> SEQ ID NO 1
<211> LENGTH: 11
<212> TYPE: DNA
<213> ORGANISM: Artificial Sequence
<220> FEATURE:
<223> OTHER INFORMATION: First Target 11-mer

<400> SEQUENCE: 1
ccaatcgtcg g                                                           11

<210> SEQ ID NO 2
<211> LENGTH: 11
<212> TYPE: DNA
<213> ORGANISM: Artificial Sequence
<220> FEATURE:
<223> OTHER INFORMATION: Second target 11-mer

<400> SEQUENCE: 2
ccccgatagc c                                                           11

<210> SEQ ID NO 3
<211> LENGTH: 11
<212> TYPE: DNA
<213> ORGANISM: Artificial Sequence
<220> FEATURE:
<223> OTHER INFORMATION: Third target 11-mer

<400> SEQUENCE: 3
ccatggctga c                                                           11

<210> SEQ ID NO 4
<211> LENGTH: 11
<212> TYPE: DNA
<213> ORGANISM: Artificial Sequence
<220> FEATURE:
<223> OTHER INFORMATION: Fourth target 11-mer

<400> SEQUENCE: 4
cccaaggcca g                                                           11

<210> SEQ ID NO 5
```

```
<211> LENGTH: 11
<212> TYPE: DNA
<213> ORGANISM: Artificial Sequence
<220> FEATURE:
<223> OTHER INFORMATION: Fifth target 11-mer

<400> SEQUENCE: 5
cccatcttgt c                                                         11

<210> SEQ ID NO 6
<211> LENGTH: 11
<212> TYPE: DNA
<213> ORGANISM: Artificial Sequence
<220> FEATURE:
<223> OTHER INFORMATION: Sixth target 11-mer

<400> SEQUENCE: 6
ccttggggaa c                                                         11

<210> SEQ ID NO 7
<211> LENGTH: 11
<212> TYPE: DNA
<213> ORGANISM: Artificial Sequence
<220> FEATURE:
<223> OTHER INFORMATION: Seventh target 11-mer

<400> SEQUENCE: 7
ccctcttgcg g                                                         11

<210> SEQ ID NO 8
<211> LENGTH: 11
<212> TYPE: DNA
<213> ORGANISM: Artificial Sequence
<220> FEATURE:
<223> OTHER INFORMATION: Eighth target 11-mer

<400> SEQUENCE: 8
ccccaaggcc a                                                         11

<210> SEQ ID NO 9
<211> LENGTH: 11
<212> TYPE: DNA
<213> ORGANISM: Artificial Sequence
<220> FEATURE:
<223> OTHER INFORMATION: Ninth target 11-mer

<400> SEQUENCE: 9
ccccggccac a                                                         11

<210> SEQ ID NO 10
<211> LENGTH: 11
<212> TYPE: DNA
<213> ORGANISM: Artificial Sequence
<220> FEATURE:
<223> OTHER INFORMATION: Tenth target 11-mer

<400> SEQUENCE: 10
ataatattgg g                                                         11

<210> SEQ ID NO 11
<211> LENGTH: 11
<212> TYPE: DNA
<213> ORGANISM: Artificial Sequence
<220> FEATURE:
<223> OTHER INFORMATION: Eleventh target 11-mer

<400> SEQUENCE: 11
```

```
ccccgaaacc c                                                            11

<210> SEQ ID NO 12
<211> LENGTH: 11
<212> TYPE: DNA
<213> ORGANISM: Artificial Sequence
<220> FEATURE:
<223> OTHER INFORMATION: Twelfth target 11-mer

<400> SEQUENCE: 12
cccaatctgc c                                                            11

<210> SEQ ID NO 13
<211> LENGTH: 11
<212> TYPE: DNA
<213> ORGANISM: Artificial Sequence
<220> FEATURE:
<223> OTHER INFORMATION: Thirteenth target 11-mer

<400> SEQUENCE: 13
ccaagtcgct c                                                            11

<210> SEQ ID NO 14
<211> LENGTH: 11
<212> TYPE: DNA
<213> ORGANISM: Artificial Sequence
<220> FEATURE:
<223> OTHER INFORMATION: Fourteenth target 11-mer

<400> SEQUENCE: 14
ccgacactga g                                                            11

<210> SEQ ID NO 15
<211> LENGTH: 11
<212> TYPE: DNA
<213> ORGANISM: Artificial Sequence
<220> FEATURE:
<223> OTHER INFORMATION: Fifteenth target 11-mer

<400> SEQUENCE: 15
cccgcatggc c                                                            11

<210> SEQ ID NO 16
<211> LENGTH: 11
<212> TYPE: DNA
<213> ORGANISM: Artificial Sequence
<220> FEATURE:
<223> OTHER INFORMATION: Sixteenth target 11-mer

<400> SEQUENCE: 16 atcggggcg g                                                             11

<210> SEQ ID NO 17
<211> LENGTH: 11
<212> TYPE: DNA
<213> ORGANISM: Artificial Sequence
<220> FEATURE:
<223> OTHER INFORMATION: Seventeenth target 11-mer

<400> SEQUENCE: 17
cctagtaaat a                                                            11

<210> SEQ ID NO 18
<211> LENGTH: 11
<212> TYPE: DNA
```

```
<213> ORGANISM: Artificial Sequence
<220> FEATURE:
<223> OTHER INFORMATION: Eighteenth target 11-mer

<400> SEQUENCE: 18
cctatctcga c                                                              11

<210> SEQ ID NO 19
<211> LENGTH: 11
<212> TYPE: DNA
<213> ORGANISM: Artificial Sequence
<220> FEATURE:
<223> OTHER INFORMATION: Nineteenth target 11-mer

<400> SEQUENCE: 19
ccggccacac c                                                              11

<210> SEQ ID NO 20
<211> LENGTH: 11
<212> TYPE: DNA
<213> ORGANISM: Artificial Sequence
<220> FEATURE:
<223> OTHER INFORMATION: Twentieth target 11-mer

<400> SEQUENCE: 20
aaggatcgcg g                                                              11

<210> SEQ ID NO 21
<211> LENGTH: 11
<212> TYPE: DNA
<213> ORGANISM: Artificial Sequence
<220> FEATURE:
<223> OTHER INFORMATION: 21st target 11-mer

<400> SEQUENCE: 21
ccgttggaag c                                                              11

<210> SEQ ID NO 22
<211> LENGTH: 23
<212> TYPE: DNA
<213> ORGANISM: Artificial Sequence
<220> FEATURE:
<223> OTHER INFORMATION: 1st target 23-mer

<400> SEQUENCE: 22
ccgacgattg gccagcaaat gga                                                 23

<210> SEQ ID NO 23
<211> LENGTH: 23
<212> TYPE: DNA
<213> ORGANISM: Artificial Sequence
<220> FEATURE:
<223> OTHER INFORMATION: 2nd target 23-mer

<400> SEQUENCE: 23
ccccgatagc cgcgccgcaa tca                                                 23

<210> SEQ ID NO 24
<211> LENGTH: 23
<212> TYPE: DNA
<213> ORGANISM: Artificial Sequence
<220> FEATURE:
<223> OTHER INFORMATION: 3rd target 23-mer

<400> SEQUENCE: 24
ccatggctga ccacgtcacc ccc                                                 23
```

```
<210> SEQ ID NO 25
<211> LENGTH: 23
<212> TYPE: DNA
<213> ORGANISM: Artificial Sequence
<220> FEATURE:
<223> OTHER INFORMATION: 4th target 23-mer

<400> SEQUENCE: 25
atcacgatca tgctggcctt ggg                                              23

<210> SEQ ID NO 26
<211> LENGTH: 23
<212> TYPE: DNA
<213> ORGANISM: Artificial Sequence
<220> FEATURE:
<223> OTHER INFORMATION: 5th target 23-mer

<400> SEQUENCE: 26
cacgcgcatc aggacaagat ggg                                              23

<210> SEQ ID NO 27
<211> LENGTH: 23
<212> TYPE: DNA
<213> ORGANISM: Artificial Sequence
<220> FEATURE:
<223> OTHER INFORMATION: 6th target 23-mer

<400> SEQUENCE: 27
ccttggggaa cgccgcacca aac                                              23

<210> SEQ ID NO 28
<211> LENGTH: 23
<212> TYPE: DNA
<213> ORGANISM: Artificial Sequence
<220> FEATURE:
<223> OTHER INFORMATION: 7th target 23-mer

<400> SEQUENCE: 28
aaccagcttg ccccgcaaga ggg                                              23

<210> SEQ ID NO 29
<211> LENGTH: 23
<212> TYPE: DNA
<213> ORGANISM: Artificial Sequence
<220> FEATURE:
<223> OTHER INFORMATION: 8th target 23-mer

<400> SEQUENCE: 29
ccccaaggcc agcatgatcg tga                                              23

<210> SEQ ID NO 30
<211> LENGTH: 23
<212> TYPE: DNA
<213> ORGANISM: Artificial Sequence
<220> FEATURE:
<223> OTHER INFORMATION: 9th target 23-mer

<400> SEQUENCE: 30
ccccggccac accagtgaca ata                                              23

<210> SEQ ID NO 31
<211> LENGTH: 23
<212> TYPE: DNA
<213> ORGANISM: Artificial Sequence
<220> FEATURE:
```

```
<223> OTHER INFORMATION: 10th target 23-mer

<400> SEQUENCE: 31
cccaatatta tgcacccggt cgc                                              23

<210> SEQ ID NO 32
<211> LENGTH: 23
<212> TYPE: DNA
<213> ORGANISM: Artificial Sequence
<220> FEATURE:
<223> OTHER INFORMATION: 11th target 23-mer

<400> SEQUENCE: 32
ccccgaaacc cggcatgtcg aga                                              23

<210> SEQ ID NO 33
<211> LENGTH: 23
<212> TYPE: DNA
<213> ORGANISM: Artificial Sequence
<220> FEATURE:
<223> OTHER INFORMATION: 12th target 23-mer

<400> SEQUENCE: 33
aaatcgcgcg atggcagatt ggg                                              23

<210> SEQ ID NO 34
<211> LENGTH: 23
<212> TYPE: DNA
<213> ORGANISM: Artificial Sequence
<220> FEATURE:
<223> OTHER INFORMATION: 13th target 23-mer

<400> SEQUENCE: 34
accgagattg ccgagcgact tgg                                              23

<210> SEQ ID NO 35
<211> LENGTH: 23
<212> TYPE: DNA
<213> ORGANISM: Artificial Sequence
<220> FEATURE:
<223> OTHER INFORMATION: 14th target 23-mer

<400> SEQUENCE: 35
ccgacactga gcactacgcc gcg                                              23

<210> SEQ ID NO 36
<211> LENGTH: 23
<212> TYPE: DNA
<213> ORGANISM: Artificial Sequence
<220> FEATURE:
<223> OTHER INFORMATION: 15th target 23-mer

<400> SEQUENCE: 36
cccgcatggc cgacaagctg cgc                                              23

<210> SEQ ID NO 37
<211> LENGTH: 23
<212> TYPE: DNA
<213> ORGANISM: Artificial Sequence
<220> FEATURE:
<223> OTHER INFORMATION: 16th target 23-mer

<400> SEQUENCE: 37
ccgcccccga tagccgcgcc gca                                              23
```

```
<210> SEQ ID NO 38
<211> LENGTH: 23
<212> TYPE: DNA
<213> ORGANISM: Artificial Sequence
<220> FEATURE:
<223> OTHER INFORMATION: 17th target 23-mer

<400> SEQUENCE: 38
attaagatca tctatttact agg                                              23

<210> SEQ ID NO 39
<211> LENGTH: 23
<212> TYPE: DNA
<213> ORGANISM: Artificial Sequence
<220> FEATURE:
<223> OTHER INFORMATION: 18th target 23-mer

<400> SEQUENCE: 39
cctatctcga catgccgggt ttc                                              23

<210> SEQ ID NO 40
<211> LENGTH: 23
<212> TYPE: DNA
<213> ORGANISM: Artificial Sequence
<220> FEATURE:
<223> OTHER INFORMATION: 19th target 23-mer

<400> SEQUENCE: 40
ccggccacac cagtgacaat atc                                              23

<210> SEQ ID NO 41
<211> LENGTH: 23
<212> TYPE: DNA
<213> ORGANISM: Artificial Sequence
<220> FEATURE:
<223> OTHER INFORMATION: 20th target 23-mer

<400> SEQUENCE: 41
ccgcgatcct tccaactcgt cgc                                              23

<210> SEQ ID NO 42
<211> LENGTH: 23
<212> TYPE: DNA
<213> ORGANISM: Artificial Sequence
<220> FEATURE:
<223> OTHER INFORMATION: 21st target 23-mer

<400> SEQUENCE: 42
ccgttggaag cgactgcccc gaa                                              23
```